United States Patent [19]

Hemphill et al.

[11] Patent Number: 4,684,612

[45] Date of Patent: Aug. 4, 1987

[54] PROCESS FOR REGENERATING SOYBEANS

[75] Inventors: John K. Hemphill, Cupertino; Eric J. Eikenberry, Atherton, both of Calif.

[73] Assignee: Sungene Technologies Corporation, Palo Alto, Calif.

[21] Appl. No.: 635,222

[22] Filed: Jul. 27, 1984

[51] Int. Cl.$^4$ .......................... C12N 5/00; C12N 5/02
[52] U.S. Cl. ............................... 435/240.5; 435/241; 435/240.54
[58] Field of Search ................................ 435/240, 241

[56] References Cited

U.S. PATENT DOCUMENTS 4,003,156  1/1977  Sibi et al. .

OTHER PUBLICATIONS

Gamborg 1984 "Plant Cell Cultures: Nutrition and Media" in *Cell Culture and Somatic Cell Genetics of Plants*, vol. 1, pp. 18–26.
Cheng et al. 1980 "Plant Regeneration from Soybean Cotyledonary Node Segments in Culture" Pl Sci Lett, v 19, 91–99.
Poehlman 1959 *Breeding Field Crops* Holt-Dryden, NY, p. 222.
*The Yearbook of Agriculture 1961* U.S. Dept. Agriculture (plate).
"Successful Induction of the Plantlets from the Callus Culture of Soya Hypocotyl" *Acta Botanica Sinica* v 18(3) 258–62, 1976.
Conger 1981, *Cloning Agricultural Plants Via in Vitro Techniques* CRC Press, pp. 11–14.
Phillips et al., Plant Cell Tissue Organ Culture 1, 123 (1981).
Wildholm et al., Plant Cell Reports 2, 19 (1983).
Gamborg et al., Plant Cell Reports 2, 209 (1983a).
Gamborg et al., Plant Cell Reports 2, 209 (1983b).
Christianson et al., Science 222, 632 (1983).
Walker et al., Plant Cell Tissue Organ Culture 1, 109 (1981).
Collins et al., in Variability in Plants Regenerating from Tissue Culture, Earle et al., Ed., pp. 22–34 (1982).
Gamborg et al., Experimental Cell Research 50, 151 (1968).

*Primary Examiner*—Thomas G. Wiseman
*Assistant Examiner*—David T. Fox
*Attorney, Agent, or Firm*—Robbins & Laramie

[57] ABSTRACT

The present invention relates to the regeneration of soybeans. The process comprises the steps of:
  (a) culturing tissue obtained from a soybean plant on a first medium comprising mineral salts, vitamins, sucrose and a hormone in an amount sufficient to ensure callus and embryoid formation;
  (b) subculturing the embryoids on a second medium comprising mineral salts, vitamins, sucrose and a hormone in an amount sufficient to ensure embryoid maturation;
  (c) subculturing the embryoids on a third medium comprising mineral salts, vitamins, sucrose and a hormone in an amount sufficient to ensure shoot formation, and
  (e) subculturing the shoots on a fourth medium comprising mineral salts, vitamins and sucrose in an amount sufficient to ensure root formation.

24 Claims, No Drawings

PROCESS FOR REGENERATING SOYBEANS

BACKGROUND OF THE INVENTION

1. Field of the Invention

The present invention relates to a general process for regenerating soybeans (*Glycine max* (L.) Merrill) and to plants produced by the process. More particularly, the invention relates to the use of tissue and cell culture for the regeneration of soybeans plantlets for many soybean varieties. The invention also relates to the media used in this process.

2. Description of the Prior Art

Plant regeneration from cells in culture is essential for the application of somatic hybridization, for the production of new varieties through somoclonal variation and for the use of genetic engineering in producing new varieties. Although plants can be regenerated from single cells of a large number of crop species, the efforts with soybean have generally been unsuccessful.

In recent years, plant cell culture successes have has a considerable influence on the respective roles of cell and organism in control of plant growth and development. This concept was supported when isolated plant cells were shown to be amenable to in vitro cultivation and complete plants could be regenerated from cultures derived from somatic cells, either directly via somatic embryogenesis or indirectly via organogenesis. Generally the regeneration pathway of choice is determined empirically by the manipulation of extrinsic factors, espceially growth regulators. Eary investigation of certain plant species have suggested that exogenous auxin concentration is the major factor controlling somatic embryogenesis, such that its reduction leads to the initiation of embryoid formation. In other species, exposure to a definite balance of auxin and cytokinin leads to the formation of organogenesis (shoots, then roots). Such manipulations, however, do not lead to plantlet formation in seed legumes (soybeans).

Despite recent successes in achieving shoot or plantlet formation from explants, callus or suspension cultures of various legumes including alfalfa, clover and *Glycine canescens*, a wild perennial special related to the soybean, plant regeneration from tissue cultures of soybean (*Glycine max*) has not been achieved in a general reproducible method which is applicable to many soybean varieties. Shoot or plantlet formation in *Glycine max* is limited to shoot production from hypocotyl slices, multiplication of cotyledonary buds and an incomplete or aberrant somatic embryogenesis. The embryogenesis from suspension culture proceeds as far as late torpedo stage. Histological examination showed, however, that the embryoids were aberrant and lacked a well-organized shoot apical meristem. Such structures are sometimes termed "neomorphs". One report has been made that plantlet formation from tissue culture was achieved for *Glycine max*. However, this report appears to have been a random event and not a general method. This report will be discussed further below.

Phillips et al., in *Plant Cell Tissue Organ Culture* 1, 123 (1981), describe the somatic embryogenesis of soybean in cell suspension or an agar. They utilized hypocotyl or epicotyl tissue for callus initiation on L2 medium. Cell suspension cultures were initiated from callus tissue in SL2 medium. The cell suspension culture could be used to produce globular and heart-shaped embryos or additional callus which could form shoot buds. The formation of somatic embryos or shoot buds was reproducible using basal SL2 or L2 media supplemented with 100 ppm casein hydroylsate, 2.25 $\mu$M 2,4-dichlorophenoxyacetic acid (2,4-D), 0.1 $\mu$M abscisic acid (ABA), 0.1 $\mu$M 2-isopropyl-4-dimethylamino-5-methylphenyl-1-piperidine carboxymethyl chloride (AMO 1618) and either 15 $\mu$M adenine or 0.46 $\mu$M kinetin. Although somatic embryos or shoot buds were formed, no plants were obtained for any varities of *Glycine max*.

Wildholm et al., in *Plant Cell Reports* 2, 19 (1983), describe the formation of shoots from *Glycine canescens* callus obtained from hypocotyls or cotyledons. Root formation did not occur, so no plantlets were obtained. The method did not produce shoots when *Glycine max* (soybean) was the source of the tissue. The formation of shoots from *Glycine canescens* tissue culture was achieved through callus induction on B5 basal medium containing 0.5 mg/l α-naphthalene acetic acid (NAA) followed in series by MS basal medium containing 0.5 mg/l of indoleacetic acid (IAA) and 5 mg/l benzyladenine (BA), and finally MS basal medium containing 0.5 mg/l BA.

Gamborg et al., in *Plant Cell Reports* 2, 209 (1983a), disclose somatic embryogenesis from cell suspension culture in several Glycine species including three cultivars (out of seven tested) of *Glycine max*. The embryoid induction medium utilized consisted of the major salts of SL, the micronutrients and vitamins of B5, 10 mg/l casamino acids, 15 $\mu$M adenine sulfate, 0.2 $\mu$M picloram and 0.025–0.25 $\mu$M AMO 1618. It was discovered that picloram was necessary for embryo induction and that it could be replaced by 0.5 to 2.0 $\mu$M 2,4-D. No embryoids were induced when the auxins NAA, IAA or indole-3-butyric acid (IBA) were utilized in place of the auxins picloram or 2,4-D. After embryoids were induced, they were transferred to embryo growth medium which consisted of SL medium containing various combinations of cytokinins (zeatin or BA), auxins (picloram) and gibberellic acid (GA$_3$). Embryoids which were formed went to a heart-shaped structure, but failed to develop beyond this stage on the induction medium. Transfer to the growth medium did result in the formation of roots, but shoots were not formed. The use of MS medium or addition of abscisic acid, coconut milk or change in osmolarity did not result in further development.

Gamborg et al., in *Plant Cell Reports* 2, 213 (1983b), describe the preparation of protoplasts from cell cultures of *Glycine tabacina* and *Glycine soja* and from leaf tissue of the soybean *Glycine max* cultivar (cv.) Williams 82. The protoplasts formed cells which could be induced to form heart-shaped embryos by the procedure of Gamborg et al. (1983a). As in the latter reference, no plantlets were formed from the procedure.

Christianson et al., in *Science* 222, 632 (1983), disclose the regeneration of a plantlet from cell suspension culture of the soybean *Glycine max* (L.) Merrill cv. Mitchell. This appears to have been the result of a random event and appears to have resulted from a piece of clonal tissue. Immature embryos were aseptically removed from 2.5–3.0 cm pods and embryo axes were cut into 1–2 mm pieces. These pieces were placed on a solid medium to induce callus formation. This medium consisted of MS salts, 0.5 mg/l nicotinic acid, 0.5 mg/l pyridoxine, 100 mg/l thiamine, 100 mg/l inositol, 2% sucrose and 5 mg/l 2,4-D. The hard, non-friable tissue was selected for transfer to new medium and resulted in a tissue line that gave rise to hard, green, glossy, abnormal embryos. When the callus tissue was transferred from the induction medium to an N-amended medium and then transferred back to the induction medium, one exceptional piece of tissue was obtained which was covered with small embryoids. The N-amended medium consisted of the induction medium in which the two nitrogen salts of the MS salts were replaced with 20 mM ammonium citrate. Transfer of the embryoids to a medium containing 0.005 mg/l IBA and 0.2 mg/l BA gave rise to shoot formation. Transfer of the shoots to a basal medium containing 0.1 mg/l of IAA resulted in root formation to produce plantlets. This procedure does not appear to be generally applicable for regenerating soybean cultivars. Instead, it appears to have been a random event which may not be reproducible. Support for this analysis lies in the source of the embryogenic tissue. Christianson et al. state that "one exceptional piece of tissue" with embryoids was obtained. Since only one was obtained out of many initiated, it implies that this was a random event and could have been clonal in nature.

The prior art does not describe a procedure for the regeneration of the soybean *Glycine max* from tissue and cell culture which is general and reproducible. The prior art does not describe a procedure which results in the formation of regenerative embryoids from the majority of calli induced instead of from a single event with a single callus. The present invention is the first instance of a broadly and generally applicable procedure for regenerating cultivars of the soybean *Glycine max*.

Soybean plants and seeds are produced by this process. The soybean plants resulting from this process may differ from the starting plant material as a result of somoclonal variation. The pathway is also useful in that it will enable the use of various selection processes to provide further variation. The plants which are produced can be used in conventional breeding programs.

SUMMARY OF THE INVENTION

The process of the present invention comprises the steps of inducing callus and embryoid formation on an induction medium from tissue of a soybean plant, maturing the embryoids on an embryoid maturation medium, forming shoots on a shoot forming medium, and forming roots on a root forming medium.

More specifically, the present process comprises the steps of:
(a) culturing tissue obtained from a soybean plant on a first medium comprising mineral salts, vitamins, sucrose and a hormone in an amount sufficient to endure callus formation and embryoid formation;
(b) subculturing the embryoids on a second medium comprising mineral salts, vitamins, sucrose and a hormone in an amount sufficient to ensure embryoid maturation;
(c) subculturing the mature embryoids on a third medium comprising mineral salts, vitamins, sucrose and a hormone in an amount sufficient to ensure shoot formation; and
(d) subculturing the shoots on a fourth medium comprising mineral salts, vitamins and sucrose in an amount sufficient to ensure root formation.

The source of the tissue is preferably immature embryos from cultivars of *Glycine max* (L.) Merrill. Suitable cutivars include Forrest, Corsoy 79, Mitchell 450, Evans, Gnome, and Northrup King variety 5-18-84-8032-23. Each basal medium preferably contains MS mineral salts, Nitsch's vitamins, myo-inositol and sucrose. Each medium utilized in the present process has a pH of 5.5–6.0.

DETAILED DESCRIPTION OF THE INVENTION

The present invention is directed to a process for regenerating soybeans (*Glycine max*) through the use of cell or tissue culture. In this process, regenerated soybean plantlets are obtained which can be placed in soil and grown to maturation. The present invention is also directed to soybean plants obtained by this process and seeds obtained from these plants.

In general, the process comprises (a) culturing soybean plant tissue on a medium to produce calli and embryoids, (b) culturing the embryoids on a medium to mature the embryoids, (c) culturing the mature embryoids on a medium to produce shoots, and (d) culturing the shoots on a medium to produce roots, which results in the formation of a plant or plantlet. Each of the media contain mineral salts, vitamins and sucrose. In addition, each medium contains a different scheme of hormones to accomplish the desired result, e.g., embryoid formation, shoot formation, etc.

The plant tissue which is preferred for use in the initiation of callus and embryoid formation is the immature embryo. The immature embryos are isolated from pods which are periodically harvested from the soybean plant. Pods are usually harvested when they reach the size of 1.5–2.5 cm in length. The pods are surface sterilized. The embryos are removed aseptically and plated onto a callus induction and embryoid formation medium, hereinafter referred to as the first medium. The embryos are 0.5–3 mm in length. It is preferred to use embryos that are 1–2 mm in length. If the embryos are smaller than 1 mm, they must be matured before plated onto the first medium.

The first medium comprises mineral salts, vitamins and sucrose. The mineral salts comprise macroelements and microelements. The macroelements used in the first medium may be the following compounds: magnesium sulfate, calcium chloride, monopotassium phosphate, potassium nitrate and ammonium nitrate. The microelements contained in the first medium are: boric acid, manganese sulfate, zinc sulfate, sodium molybdate (VI), copper (II) sulfate, cobalt chloride, potassium iodide, iron (II) sulfate and disodium EDTA. This combination of mineral salts is known in the art as the MS mineral salts. In the first medium, the MS mineral salts have been modified so that the medium contains more iron and EDTA than the standard MS mineral salts.

The preferred amounts of the macroelements and microelements used to prepare one liter of the first medium are as follows: 370 mg magnesium sulfate heptahydrate, 440 mg calcium chloride dihydrate, 170 mg monopotassium phosphate, 1900 mg potassium nitrate, 1650 mg ammonium nitrate, 6.2 mg boric acid, 16.9 mg manganese sulfate monohydrate, 8.6 mg zinc sulfate heptahydrate, 0.25 mg sodium molybdate (VI) dihydrate, 0.025 mg copper (II) sulfate pentahydrate, 0.025 mg cobalt chloride hexahydrate, 0.83 mg potassium iodide, 41.7 mg iron (II) sulfate heptahydrate, and 55.9 mg disodium EDTA.

The first medium also contains vitamins. The vitamins used include myo-inositol, nicotinic acid, glycine, pyridoxine, thiamine, folic acid and biotin. These vitamins, exclusive of myo-inositol, are known in the art as Nitsch's vitamins. The Nitsch's vitamins have been modified so that they contain more thiamine.

The amounts of vitamins used to prepare one liter of the first medium are as follows: 100 mg myo-inositol, 5 mg nicotinic acid, 2 mg glycine, 0.5 mg pyridoxine hydrochloride, 0.9 mg thiamine hydrochloride, 0.5 mg folic acid and 0.05 mg biotin.

The first medium contains 2%–3% sucrose, preferably 2%, and a gelling substance such as agar or Gelrite TM (trademark, Kelco Commercial Development). It is preferred to use Gelrite TM at a concentration of 0.2%. The medium has a pH of 5.5–6.0 with a preferred pH of 5.8.

In addition to the above components, the first medium also contains a hormone. It has been found that the hormone which is useful for callus induction and embryoid formation may be selected from the group comprising 2,4-D or a mixture of IAA and 2,4-D. The amount of hormone that is present is sufficient to ensure callus and embryoid formation. Generally, 0.5–10 mg/l 2,4-D or 1–3 mg/l IAA in combination with 3–10 mg/l 2,4-D is sufficient. Preferably, 3–10 mg/l 2,4-D, 1–3 mg/l IAA in combination with 3 mg/l 2,4-D or 3 mg/l IAA in combination with 3 mg/l, 5 mg/l or 10 mg/l 2,4-D is utilized as the hormone in the first medium. It is also possible to add ABA to the mixture of IAA and 2,4-D. For this, it is preferred to utilize 0.0264–0.264 mg/l, preferably 0.264 mg/l, ABA with the above combinations of IAA and 2,4-D. The medium is sterilized by autoclaving all of the components except IAA, which is sterilized by microporous membrane filtration.

The immature embryos are plated on the first medium and cultured in the light for 7–70 days. During this time the embryo undergoes de-differentiation, callus formation and embryoid formation. The callus and embryoids are generally transferred depending on the condition of the callus and the maturation of the embryoids. The condition of the callus and the maturation of the embryoids are judged by the coloration and shape of the tissue. It is preferred to obtain a light green embryoid which undergoes the regular steps of normal embryo growth. If an embryoid appears to be declining, it is transferred. Thus, an embryoid is transferred if it becomes pale green or white, or if it does not appear to progress normally. The callus with embryoids can be transferred to fresh medium if the growth is slow.

If the immature embryo is less than 1 mm in length, it is preferred to mature the embryo before plating it on the first medium. This maturation is accomplished by growing the embryo on an embryo growth medium. The embryo growth medium comprises mineral salts, vitamins, amino acids and sucrose. The mineral salts are as described for the first medium. The vitamins are as described for the first medium except that 4000 mg/l of myo-inositol is used in the embryo growth medium.

The embryo growth medium also contains amino acids. The amino acids are alanine, glutamine, serine, tryptophan, proline and arginine. All amino acids are in the L-form unless otherwise indicated. The preferred amounts of amino acids used to prepare one liter of medium are: 1000 mg alinine, 800 mg glutamine, 160 mg serine, 50 mg tryptophan, 575 mg proline and 870 mg arginine. It is also possible to use one-half the amount of these amino acids.

The embryo growth medium contains 10%–12% sucrose and a gelling substance such as agar or Gelrite TM. It is preferred to use Gelrite TM at 0.2% concentration. The medium has a pH of 5.5–6.0, with 5.8 preferred.

The embryo growth medium further contains a hormone. It has been found that the hormone which is useful for embryo growth is a mixture of IAA, adenine sulfate and ABA, or a mixture of IAA, t-zeatin and ABA. 0.1–0.5 mg/l IAA, 0.1–1.0 mg/l adenine sulfate and 0.264–1.32 mg/l ABA or 0.1–0.5 mg/l IAA, 0.1–0.5 mg/l t-zeatin and 0.264–1.32 mg/l ABA may be used. It is preferred to use either 0.1 mg/l IAA, 1 mg/l adenine sulfate and 1.32 mg/l ABA or 0.1 mg/l IAA, 0.2 mg/l t-zeatin and 1.32 mg/l ABA as the hormone in the embryo growth medium. If the hormone is IAA, adenine sulfate and ABA, it is preferred to use 12% sucrose and full-strength amino acid mixture. For the other hormone combination, it is preferred to use 10% sucrose and either full- or half-strength amino acid mixture.

The medium is sterilized by autoclaving all of the components except the IAA and t-zeatin which are sterilized by membrane filtration. The embryos are grown on this medium in the light until they reach the 1–2 mm size, at which time they are plated onto the first medium.

After culturing the embryo on the first medium, the embryoids can be matured by transferring and subculturing them on a maturation medium, hereinafter referred to as the second medium. The callus with the embryoids is subcultured on the second medium in the light for 20–75 days, preferably for about 30 days. It may be necessary to transfer the maturing embryoids to fresh medium during this time period in order to obtain complete maturation.

The second medium which can be utilized to mature the embryoids may be selected from a group consisting of five different media, hereinafter referred to as second medium A–E. Each second medium contains 2%–3%, preferably 2%, sucrose and a gelling substance, preferably 0.2% Gelrite TM. The pH is 5.5–6.0, and preferably 5.8. Each medium is sterilized by autoclaving except that IAA and t-zeatin are sterilized by membrane filtration.

Second medium A comprises the first medium which has been preconditioned. The first medium is preconditioned by the growing callus with its embryoids. When this medium is utilized, the callus is transferred to a position 1–2 cm (preferably 1 cm) away from its original position.

Second medium B comprises mineral salts, vitamins and a hormone. The mineral salts and vitamins are the same as used in the first medium. The hormone which may be utilized is selected from the following group: (1) 3–5 mg/l, preferably 5 mg/l, 2,4-D; (2) 1–3 mg/l, preferably 2 mg/l, IAA and 3–5 mg/l, preferably 3 mg/l 2,4-D; (3) 1.0–2.0 mg/l, preferably 1 mg/l, IAA and 0.5–1.0 mg/l, preferably 1 mg/l, t-zeatin; (4) 1.0–2.0 mg/l, preferably 1 mg/l, IAA and 2.73–5.46 mg/l, preferably 5.46 mg/l, adenine sulfate; and (5) 3–5 mg/l, preferably 3 mg/l, 2,4-D, 1–3 mg/l, preferably 2 mg/l, IAA and 0.0264–0.264 mg/l, preferably 0.264 mg/l ABA.

Second medium C comprises mineral salts, vitamins, casein hydrolysate and a hormone. The mineral salts and vitamins are the same as used in the first medium. The casein hydrolysate is an enzymatic hydrolysis of casein that is commercially available and well known in the art. It is present in the amount of 100–1000 mg/l, preferably 100 mg/l. The hormone used in this medium is a mixture of 1.0–2.0 mg/l IAA, 0.5–1.0 mg/l t-zeatin, 0.0097–0.0606 mg/l picloram and 0.0264–1.32 mg/l ABA. It is preferred to use 1 mg/l IAA, 1 mg/l t-zeatin, either 0.0097 or 0.0606 mg/l picloram, and 0.0264 mg/l ABA.

Second medium D comprises mineral salts, vitamins and a hormone. The vitamins are the same as used in the first medium, except that the Nitsch's vitamins are not modified. That is, only 0.5 mg/l thiamine hydrochloride is used. The mineral salts are the same as in the first medium, except that ammonium citrate is used in place of the potassium nitrate and the ammonium nitrate. The ammonium citrate is preferably used in an amount of 20 mM. The hormone is 1.0–2.0 mg/l, preferably 1 mg/l, IAA and 2.73–5.46 mg/l, preferably 2.73 mg/l, adenine sulfate.

The second medium E comprises mineral salts, vitamins, casein hydrolysate and a hormone. The mineral salts and vitamins are the same as used in second medium D. The casein hydrolysate is the same as used in second medium C. The hormone utilized in this medium contains 1.0–2.0 mg/l IAA, 0.5–1.0 mg/l t-zeatin, 0.0097–0.0606 mg/l picloram and 0.0264–1.32 mg/l ABA. It is preferred to use 1 mg/l IAA, 1 mg/l t-zeatin, 0.0097 mg/l picloram and 0.0264 mg/l ABA.

If it is necessary because of slow maturation to transfer the maturing embryoids to fresh medium, it is preferred to use one of the media which was not utilized for the initial maturation. For example, if second medium A was first used, it is preferred to then use any of second mediums B–E if necessary. Generally, the embryiods are subcultured on each second medium which is used for 20–75 days, preferably about 30 days, in the light.

After growth on the second medium, the mature embryoids are then transferred to a shoot formation medium, hereinafter referred to as the third medium. The third medium contains the same mineral salts and vitamins as the first medium. In addition, this medium contains a hormone to ensure shoot formation. It has been found that a mixture of IBA and BA or a mixture of IAA and adenine sulfate is useful for shoot formation. Generally, 0.001–0.05 mg/l IBA and 0.1–0.5 mg/l BA or 1.0–3.0 mg/l IAA and 2.73–10.92 mg/l adenine sulfate are utilized. It is preferred that 0.005 mg/l IBA and 0.2 mg/l BA or 3 mg/l IAA and either 5.46 mg/l or 10.92 mg/l adenine sulfate be used. It has also been found that the addition of gibberellic acid to the IBA and BA mixture enhances shoot elongation and maturation in slow-growing embryoids. It is preferred to use 0.03464 mg/l gibberallic acid in this instance. It has further been found that a mixture of 0.05 mg/l of IAA, 0.05 mg/l of BA and 0.03464 mg/l $GA_3$ can be used for this maturation.

It is preferred that the third medium contains the same amounts of sucrose, i.e., 2%–3%, preferably 2%, and gelling substance as the first medium. This medium is also sterilized by autoclaving, except for the IAA and $GA_3$ which are sterilized by membrane filtration.

Once shoots have formed, they are transferred to a root formation medium, hereinafter referred to as the fourth medium. This transfer is usually made after the embryoids have been subcultured on the third medium for 20–80 days, and preferably after about 30 days. It may be necessary to transfer the material to fresh medium during this time period. If transfers are made, these may be done after 30–45 days, preferably after 30 days. Transferring is usually done if the shoots have not elongated properly. That is, if the shoots do not have two sets of leaves, they are transferred to fresh third medium or onto a modified third medium containing one-half the concentration of the mineral salts and reduced thiamine and myo-inositol, with the other components being the same, before they are placed on the fourth medium. If gibberllic acid is being utilized, it is preferred to use the modified third medium. It is further preferred to use $GA_3$ for the maturation.

The root formation medium may or may not contain any hormones. It contains the same mineral salts and vitamins as the first medium. When a hormone is present, 0.1–1.0 mg/l IBA or 0.1–1.0 mg/l IAA is used. Preferably, 0.5 mg/l of IBA or IAA is utilized. If the modified third medium is used prior to transfer to the fourth medium, it is preferred to use a modified fourth medium containing one-half the concentration of the mineral salts and reduced thiamine and myo-inositol, with the other components remaining the same. The fourth medium also includes a gelling substance such as agar or Gelrite ™. It is preferred to use Gerlrite ™ at a concentration of 0.25%. 1%–3%, preferably 2%, sucrose is utilized. This medium has a pH of 5.5–6.0, with 5.8 preferred. The medium is sterilized by autoclaving except when IAA is utilized. The IAA is sterilized as previously described.

After the roots have formed, the plantlets are ready to be potted in soil. This is generally done after the shoots have been subcultured on the fourth medium in the light for 20–60 days, preferably for about 30 days. It may be necessary to transfer the material to fresh medium during this time period. The transfer can be to fresh fourth medium or to a modified fourth medium in which all the components are present at one-half the concentration in the original fourth medium. The plantlets are potted by transferring the plantlets to soil which is well moistened and contained in a high humidity chamber. Once the plantlets are established, they are removed from the high humidity chamber, transplanted to soil, and grown to maturity to produce seeds.

This process is useful for regenerating plantlets from tissue of many cultivars of soybean. The process is useful for regenerating plantlets from *Glycine max* (L.) Merrill cv. Forrest, Corsoy 79, Mitchell 450, Evans, Gnome and Northrup King variety S-18-84-8032023. It has been found that more transfers are required for the slow growers, i.e., embryoids which are progressing slowly along the normal developmental path.

The present invention will be further described by reference to the following non-limiting examples. In these examples, culturing in the light refers to culturing in light having a photoperiod of 16 hours per day at 25°–29° C. unless indicated otherwise. The temperature during the 8 hour dark phase is 23°–24° C. unless indicated otherwise.

EXAMPLE 1

Preparation of Solutions

The following stock solutions or solutions were prepared for use in making the media described in further detail below.

1. Mineral Salts

A. Iron and EDTA Modified MS

The solution was prepared immediately before use by dissolving one packet of Murashige minimal organics medium without sucrose (Gibco Laboratories catalog No. 510-3118) in 800 ml of distilled, deionized water. A small amount of distilled, deionized water was used to rinse out the packet. Additionally, 5 ml of the iron and EDTA stock solution was added. The packaged medium contained 100 mg myo-inositol and 0.4 mg thiamine hydrochloride.

B. Iron and EDTA Modified One-Half Strength MS

The solution was prepared immediately before use by dissolving one-half packet of Murashige minimal organics medium without sucrose in the manner described above. 10 ml of the iron and EDTA stock solution was used. The packaged medium contained 100 mg myo-inositol and 0.4 mg thiamine hydrochloride, so the final amount was 50 mg myo-inositol and 0.2 mg thiamine hydrochloride.

C. Ammonium Citrate, Iron and EDTA Modified MS

The solution was prepared immediately before use by adding 20 ml of the myo-inositol stock solution, 10 ml of the MS minor salts stock solution, 15 ml of the iron and EDTA stock solution, and 100 ml of the calcium chloride stock solution to 100 ml of the ammonium citrate modified MS major salts stock solution. The stock solutions not described elsewhere were prepared as follows.

(1) A 50X stock solution of myo-inositol was prepared by dissolving 2500 mg of myo-inositol in 500 ml of distilled, deionized water.

(2) A 100X stock solution of the MS minor salts was prepared by dissolving the following components in 500 ml of distilled, deionized water.

| Component | Weight (mg) | Component | Weight (mg) |
|---|---|---|---|
| $ZnSO_4.7H_2O$ | 430 | KI | 41.5 |
| $Na_2MoO_4.2H_2O$ | 12.5 | $H_3BO_3$ | 310 |
| $CuSO_4.5H_2O$ | 1.25 | $MnSO_4.H_2O$ | 845 |
| $CoCl_2.6H_2O$ | 1.25 | | |

(3) A 10X stock solution of the ammonium citrate modified MS major salts was prepared by dissolving 3.7 g of magnesium sulfate heptahydrate, 1.7 g of monopotassium phosphate and 45.24 g of diammonium citrate in 1000 ml of distilled, deionized water.

(4) A 10X stock solution of calcium chloride was prepared by dissolving 4.4 g of calcium chloride dihydrate in 1000 ml of distilled, deionized water.

2. Vitamins

The 100X stock solution of vitamins was prepared by dissolving the following components in 500 ml of distilled, deionized water.

| Component | Weight (mg) | Component | Weight (mg) |
|---|---|---|---|
| nicotinic acid | 250 | thiamine.HCl | 25 |
| glycine | 100 | folic acid | 25 |
| pyridoxine.HCl | 25 | biotin | 2.5 |

3. Amino Acids

A 50X stock solution of amino acids was prepared by dissolving the following components in 500 ml of distilled, deionized water.

| Component | Weight (mg) | Component | Weight (mg) |
|---|---|---|---|
| alanine | 25 | tryptophan | 1.25 |
| glutamine | 20 | proline | 14.375 |
| serine | 4 | arginine | 21.75 |

The stock solution was frozen in 10 ml aliquots until used to prepare the media.

4. Iron and EDTA

A 100X stock solution of iron and EDTA was prepared by dissolving 1.39 g of iron (II) sulfate heptahydrate and 1.86 g of disodium-EDTA in 500 ml of distilled, deionized water.

5. Hormones (A) A 0.264 mg/ml stock solution of ABA was prepared by dissolving 26.4 mg of ABA in 20 ml of 1M $NaHCO_3$ and diluting to 100 ml with distilled, deionized water.

(B) A 1 mg/ml stock solution of BA was prepared by dissolving 100 mg of BA in 20 ml of 1N NaOH and diluting to 100 ml with distilled, deionized water.

(C) A 1 mg/ml stock solution of 2,4-D was prepared by dissolving 100 mg of 2,4-D in 20 ml of 70% ethanol and diluting to 100 ml with distilled, deionized water.

(D) A 1 mg/ml stock solution of IBA was prepared by dissolving 100 mg of IBA in 20 ml of 70% ethanol and diluting to 100 ml with distilled, deionized water.

(E) A 2.73 mg/ml stock solution of adenine sulfate was prepared by dissolving 273 mg of adenine sulfate in 20 ml of 1N NaOH and diluting to 100 ml with distilled, deionized water.

(F) A 1 mg/ml stock solution of t-zeatin was prepared by dissolving 100 mg of t-zeatin in 5 ml of 5N HCl and diluting to 100 ml with distilled, deionized water.

(G) A 0.00024 mg/ml stock solution of picloram was prepared by dissolving 0.024 mg of picloram in 20 ml of warm, distilled water and diluting to 100 ml with distilled, deionized water.

(H) A 1 mg/ml stock solution of IAA was prepared by dissolving 100 mg of IAA in 20 ml of 70% ethanol and diluting to 100 ml with distilled, deionized water. The stock solution was stored in a bottle wrapped in aluminum foil in a refrigerator. The solution was prepared fresh every 1 to 2 months.

(I) A 0.346 mg/ml stock solution of $GA_3$ was prepared by dissolving 34.6 mg of $GA_3$ in 20 ml of absolute ethanol and diluting to 100 ml with distilled, deionized water.

EXAMPLE 2

Preparation of Media

1. Embryo Growth Medium

The embryo growth medium was prepared by adding 20 ml of the amino acid stock solution and 10 ml of the vitamin stock solution to the iron and EDTA modified MS. 120 gm of sucrose and 2 gm Gelrite TM were dissolved in this mixture. 5 ml of the ABA stock solution and 0.37 ml of the adenine sulfate stock solution were added, and the volume brought to one liter with distilled, deionized water. The pH was adjusted to 5.8 using 1N HCl or 1N NaOH. The mixture was then autoclaved at 18 psi for 15 minutes. While the medium was cooling, 0.1 ml of the IAA stock solution which was sterilized by passing through a 0.22μ Millipore membrane was added. The medium was then poured into petri dishes.

To change the concentration of the hormones in the growth medium, the amounts of the stock solutions utilized were adjusted accordingly. For example, if 0.528 mg/l ABA was desired instead of 1.32 mg/l, 2 ml of the ABA stock solution was used. If t-zeatin was used in place of adenine sulfate, the appropriate amount was added to the cooling medium after sterilization, which was accomplished by membrane filtration as for IAA. For example, if 0.2 mg/l was desired, then 0.2 ml of the t-zeatin stock solution was used.

2. First Medium or Callus and Embryoid Formation Medium

The first medium was prepared by adding 10 ml of the vitamin stock solution to the iron and EDTA modified MS. 20 gm of sucrose and 2 gm of Gelrite ™ were dissolved in this mixture. 0.5 ml of the 2,4-D stock solution was added and the volume brought to one liter with distilled, deionized water. The pH was adjusted to 5.8 with 1N HCl or 1N NaOH. The mixture was autoclaved at 18 psi for 15 minutes. The cooling medium was poured into petri dishes.

To prepare the first medium having different concentrations of 2,4-D, the amount of the stock solution utilized was adjusted accordingly. For example, if 10 mg/l 2,4-D was desired instead of 0.5 mg/l, then 10 ml of the 2,4-D stock solution was used.

To prepare the first medium containing a mixture of 2,4-D and IAA as the hormone, or a mixture of IAA, ABA and 2,4-D, the amount of 2,4-D or the amount of 2,4-D and ABA to give the desired concentration was added as described above. The IAA stock solution was sterilized as described above and added to the cooling medium in an amount to give the desired concentration. For example, if the desired concentrations were 3 mg/l 2,4-D and 2 mg/l IAA, then 3 ml of the 2,4-D stock solution was added to the medium and 2 ml of the IAA stock solution was added to the cooling medium.

3. Second Medium or Embryoid Maturation Medium

A. Second Medium A

Second medium A was prepared by preconditioning the first medium. The first medium was prepared as described above. Embryos were plated on the first medium and grown for 30 days. Second medium A was the medium within 1-2 cm of the callus growth.

B. Second Medium B

Second medium B was prepared by adding 10 ml of the vitamin stock solution to the iron and EDTA modified MS. 20 gm of sucrose and 2 gm of Gelrite ™ were dissolved in this mixture. 5 ml of the 2,4-D stock solution was added, and the volume brought to one liter with distilled, deionized water. The pH was adjusted to 5.8 with 1N HCl or 1N NaOH. The mixture was autoclaved at 18 psi for 15 minutes. The cooling medium was poured into petri dishes.

To prepare second medium B having different concentrations of 2,4-D, the amount of the stock solution utilized was adjusted accordingly. For example, if 3 mg/l 2,4-D was desired instead of 5 mg/l, then 3 ml of the 2,4-D stock solution was used.

To prepare the second medium B containing a mixture of 2,4-D and IAA or a mixture of IAA, 2,4-D and ABA as the hormone, an amount of 2,4-D or an amount of 2,4-D and of ABA to give the desired concentration was added as described above. The IAA stock solution was sterilized as described above and added to the cooling medium in an amount to give the desired concentration. For example, if the desired concentrations were 3 mg/l 2,4-D and 2 mg/l IAA, then 3 ml of the 2,4-D stock solution was added to the medium and 2 ml of the IAA stock solution was added to the cooling medium.

To prepare the second medium B containing a mixture of IAA and t-zeatin as the hormone, the medium was prepared as described above except that the 2,4-D stock solution was not added. The stock solution of IAA and the stock solution of t-zeatin were each sterilized by membrane filtration as described above for IAA and added to the cooling medium in an amount to give the desired concentration. For example, if the desired concentrations were 1 mg/l IAA and 1 mg/l t-zeatin, then 1 ml of the IAA stock solution and 1 ml of the t-zeatin stock solution were added to the cooling medium.

To prepare the second medium B containing a mixture of IAA and adenine sulfate as the hormone, the medium was prepared as described above, except that the desired amount of the adenine sulfate stock solution was added instead of the 2,4-D stock solution. The sterilized IAA stock solution was added in the desired amount to the cooling medium. For example, if desired concentrations were 1 mg/ml IAA and 5.46 mg/l adenine sulfate, then 2 ml of the adenine sulfate stock solution was added in the preparation of the medium before autoclaving and 1 ml of the sterilized IAA stock solution was added to the cooling medium.

C. Second Medium C

Second medium C was prepared by adding 10 ml of the vitamin stock solution to the iron and EDTA modified MS. 20 gm of sucrose, 100 mg of casein hydrolysate (Difco ® brand vitamin free casamino acid) and 2 mg of Gelrite ™ were added to this mixture. 0.25 ml of the picloram stock solution and 0.1 ml of the ABA stock solution were added, and the volume brought to one liter with distilled, deionized water. The pH was adjusted to 5.8 with 1N HCl or 1N NaOH as judged by pH paper. The mixture was autoclaved at 18 psi for 15 minutes. 1 ml of the IAA stock solution and 1 ml of the t-zeatin stock solution, each sterilized as described above, were added to the cooling medium which was then poured into petri dishes.

Second medium C, having different concentrations of the hormone components were prepared in the analogous manner as previously described for the other media compositions.

D. Second Medium D

Second medium D was prepared by adding 10 ml of the vitamin stock solution to the ammonium citrate, iron and EDTA modified MS. 20 gm of sucrose and 2 gm of Gelrite ™ were dissolved in this mixture. 1 ml of the adenine sulfate stock solution was added, and the volume brought to one liter with distilled, deionized water. The pH was adjusted to 5.8 with 1N HCl or 1N NaOH. The mixture was autoclaved at 18 psi for 15 minutes. 1 ml of the IAA stock solution, sterilized as previously described, was added to the cooling medium which was then poured into petri dishes. If it was desired to alter the IAA and adenine sulfate concentrations in second medium D, this was accomplished in the manner previously described.

E. Second Medium E

Second medium E was prepared as described for second medium C, except that the ammonium citrate, iron and EDTA modified MS was used in place of the iron and EDTA modified MS of second medium C.

4. Third Medium or Shoot Formation Medium

The third medium was prepared by adding 10 of the vitamin stock solution to the iron and EDTA modified MS. 20 gm of sucrose and 2 gm of Gelrite ™ were dissolved in this mixture. 0.2 ml of the BA stock solution and 0.005 ml of the IBA stock solution were added, and the volume brought to one liter with distilled, deionized water. The pH was adjusted to 5.8 with 1N HCl or 1N NaOH. The mixture was then autoclaved at 18 psi for 15 minutes, and the cooling medium was poured into petri dishes. If it was desired to alter the IBA and BA concentrations, this was accomplished in the manner previously described.

To prepare the third medium containing IAA and adenine sulfate instead of BA and IBA, 4 ml of the adenine sulfate stock solution was added in place of the BA and IBA. 3 ml of the IAA stock solution, sterilized as previously described, was added to the cooling medium before pouring into petri dishes. The concentrations were altered, if desired, as previously described.

This medium was also prepared using the iron and EDTA modified one-half strength MS in place of the iron and EDTA modified MS.

5. Fourth Medium or Root Formation Medium

The fourth medium was prepared by adding 10 ml of the vitamin stock solution to the iron and EDTA modified MS. 20 gm of sucrose and 2.5 mg of Gelrite TM were dissolved in this mixture, and the volume was brought to one liter with distilled, deionized water. The pH was adjusted to 5.8 with 1N HCl or 1N NaOH. The mixture was sterilized by autoclaving at 18 psi for 15 minutes. The cooling medium was poured into petri dishes.

This medium was also prepared using the iron and EDTA modified one-half strength MS in place of the iron and EDTA modified MS.

EXAMPLE 3

Soybean Regeneration

Immature embryos were isolated from pods of the soybean, *Glycine max* (L.) Merrill cv. Evans, when the pods were 1.5 to 2.5 cm in length. This variety of soybean was obtained from Dr. Nickell of the College of Agriculture, Department of Agronomy, University of Illinois, Urbana, Ill. The soybean pods were collected each morning and placed in a sterile 18 oz. bottle. Surface sterilizing agents employed separately were as follows: 70% ethanol (1 min.), 50% concentrated Clorox TM (8 min.), and washing three times with distilled, deionized water. Sterile pods were placed in the top of a sterile petri dish (100 mm×25 mm). Each pod was individually cut with scissors. The ovules (3 to 4 per pod) were carefully pressed out of the pod into the bottom petri dish (sterile). A pair of forceps and a needle probe were used to take out the immature embryo from each ovule. The embryos were plated onto the first medium contained in a petri dish. This medium was prepared as described above, using 0.5 mg 2,4-D as the hormone. The petri dish was placed in the light and cultured for 70 days to form calli and embryoids.

At this time, each callus with embryoids was transferred to second medium C which was prepared as described above, using 1 mg/l t-zeatin, 1 mg/l IAA, 0.0606 mg/l picloram and 0.0264 mg/l ABA. The callus was cultured on this medium for 72 days in the light.

The callus with mature embryoids was then transferred to a second medium D prepared as described in Example 2, using 1 mg/l IAA and 2.73 mg/l adenine sulfate. The callus with embryoids was cultured on this medium for 46 days in the light. The embryoids formed shoots.

The callus with the shoots were transferred to the fourth medium contained in petri dishes, and prepared as described above. The shoots were cultured on this medium for 30 days in the light. During this time, the shoot formed roots.

The Gelrite TM was washed off the roots of the plantlet with distilled, deionized water. The plantlet was then transferred to soil in a quart Mason jar. The bottom of the Mason jar was covered with sterile, activated charcoal. Four inches of an autoclaved, equal mixture of vermiculite, perlite and potting soil was placed over the charcoal. The plantlet was planted in the soil and the soil was well moistened with distilled, deionized water. Parafilm TM was placed over the jar and the cap was screwed over the Parafilm TM. The jar was then placed in a Percival growth chamber at 24° C., having a photoperiod of 16 hours per day. After 12 days, the jar was removed from the growth chamber and placed in a sweater box in the greenhouse. A second sweater box was placed perpendicular over the first sweater box and a paper towel was placed over it to provide for diffuse sunlight. The greenhouse had a temperature of 29° C.±3° C. during the day and 21° C.±2° C. during the night, and a photoperiod of 16 hours per day. After one week, the Parafilm TM was removed from the jar. Four days later, the regenerated plant was transplanted to a 6" pot containing an equal mixture of vermiculite, perlite and potting soil, and returned to the sweater boxes. The regenerated plant flowered and formed pods which contained developing ovules.

EXAMPLE 4

Soybean Regeneration

Immature embryos were isolated as in the previous example and plated on the first medium containing 10 mg/l 2,4-D. The plates were cultured for seven days in the light. The callus with embryoids were then transferred to second medium B containing 2 mg/l IAA, 0.264 mg/l ABA and 3 mg/l 2,4-D, and cultured for 38 days in the light.

At this time, each callus with embryoids was transferred to second medium B containing 1 mg/l IAA and 5.46 mg/l adenine sulfate. The plates were cultured in the light at 25°-29° C. for 34 days. At this time, each callus with mature embryoids was transferred to third medium containing 0.2 mg/l BA and 0.005 mg/l IBA. The plates were cultured in the light for 29 days before each callus with shoots was transferred to the fourth medium.

After 27 days of culturing in the light, the plantlets were removed and placed in a quart Mason jar as previously described. The jar was then placed in a Percival growth chamber at 24° C., and having a photoperiod of 16 hours per day.

EXAMPLE 5

Soybean Regeneration

Immature embryos from *Glycine max* (L.) Merrill cv. Northrup King variety S-18-84-8032-23 were isolated as previously described and plated on the first medium containing 2.0 mg/l 2,4-D. The plates were cultured in the light for 58 days. Each callus with embryoids was then transferred to second medium B containing 1 mg/l IAA and 1 mg/l t-zeatin. After 47 days of culturing in the light, each callus with mature embryoids was transferred to the third medium containing 3 mg/l IAA and 5.46 mg/l adenine sulfate, and cultured in the light for 47 days. At this time, each callus with shoots was transferred to the fourth medium and cultured in the light for 58 days. The plantlets were then removed and placed in a quart Mason jar as previously described. The jar was then placed in a Percival growth chamber.

EXAMPLE 6

Soybean Regeneration

Immature embryos from *Glycine max* (L.) Merrill cv. Corsoy 79 were isolated as previously described. This cultivar was obtained from Dr. Nickell. The embryos were plated on the first medium containing 10 mg/l 2,4-D, and cultured in the light for 10 days. Each callus with embryoids was then transferred to second medium B containing 5 mg/l 2,4-D, and cultured in the light. After 20 days, each callus with embryoids was transferred to second medium E containing 1 mg/l IAA, 1 mg/l t-zeatin, 0.0097 mg/l picloram and 0.0264 mg/l ABA, and cultured in the light for 52 days. Each callus with mature embryoids was then transferred to third medium containing 3 mg/l IAA and 10.92 mg/l adenine sulfate. After culturing in the light for 45 days, each callus with developing shoots was transferred to third medium containing 0.2 mg/l BA and 0.005 mg/l IBA for shoot elongation. These were cultured for 31 days in the light and then transferred to the fourth medium. The callus containing shoots were cultured in the light on this medium to form roots.

EXAMPLE 7

Soybean Regeneration

Immature embryos were isolated as described in Example 6 and plated onto first medium containing 10 mg/l 2,4-D. They were cultured for eight days in the light before being transferred to second medium B containing 2 mg/l IAA and 3 mg/l 2,4-D. Each callus with embryoids was matured on this medium by culturing in the light for 37 days. Each callus with mature embryoids was transferred to the third medium containing 0.2 mg/l BA and 0.005 mg/l IBA. Culturing on this medium was performed for 63 days in the light with a transfer to fresh medium after 32 days. Each callus containing developing shoots was then placed on third medium containing one-half the concentration of the Murashige minimal organics. These were cultured in the light on this medium for shoot elongation.

EXAMPLE 8

Soybean Regeneration

Immature embryos were isolated as described in Example 6 and plated onto first medium containing 10 mg/l 2,4-D. After eight days of culturing in the light, each callus with embryoids was transferred to second medium B containing 2 mg/l IAA and 3 mg/l 2,4-D. These were cultured in the light for 37 days, and then transferred to second medium E containing 1 mg/l IAA, 1 mg/l t-zeatin, 0.0097 mg/l picloram and 0.0264 mg/l ABA. Each callus with mature embryoids was transferred after 32 days to the third medium containing 0.2 mg/l BA and 0.005 mg/l IBA. After culturing for 31 days in the light, each callus with developing shoots was transferred to third medium containing one-half the concentration of the Murashige minimal organics. These were cultured in the light on this medium for shoot elongation.

EXAMPLE 9

Soybean Regeneration

Immature embryos from *Glycine max* (L.) Merrill cv. Forrest were isolated as previously described. This cultivar was obtained from Dr. Hartwig at the U.S. Department of Agriculture, Agricultural Research Service, Soybean Production Research, Stoneville, Miss. The embryos were plated on first medium containing 2.0 mg/l 2,4-D and cultured in the light for 48 days. Each callus with embryoids was then transferred to second medium D containing 1 mg/l IAA and 2.73 mg/l adenine sulfate. After culturing on this medium in the light for 55 days, each callus with mature embryoids was transferred to third medium containing 0.2 mg/l BA and 0.005 mg/l IBA. These were cultured on this medium for 37 days in the light. Each callus with shoots was then transferred to the fourth medium and cultured in the light for 13 days. At this time they were transferred to fourth medium having one-half the concentration of mineral salts, vitamins and sucrose, and cultured in the light for root formation.

EXAMPLE 10

Soybean Regeneration

Immature embryos from *Glycine max* (L.) Merrill cv. Gnome was isolated as previously described. This cultivar was obtained from Dr. Nickell. The embryos were plated on first medium containing 5 mg/l 2,4-D and cultured in the light for 56 days. Each callus with embryoids was then transferred to second medium E containing 1 mg/l IAA, 1 mg/l t-zeatin 0.00097 mg/l picloram and 0.0264 mg/l ABA. After culturing in the light for 59 days, each callus with mature embryoids was transferred to third medium containing 0.2 mg/l BA and 0.005 mg/l IBA. Culturing on this medium was performed for 77 days in the light, with a transfer to fresh medium after 43 days. Each callus containing developing shoots was then placed on third medium containing one-half the concentration of the Murashige minimal organics and 1% surcose. These were cultured in the light for shoot elongation.

EXAMPLE 11

Soybean Regeneration

Immature embryos less than 10 mm were isolated from *Glycine max* (L.) Merrill cv. Evans as previously described. The embryos were plated on the embryo growth medium containing 0.1 mg/l IAA, 1 mg/l adenine sulfate and 1.32 mg/l ABA, prepared as described above using 20 ml of the amino acid mixture and cultured in the light for 21 days. Each callus with embryoids was then transferred to second medium B containing 3 mg/l IAA, 3 mg/l 2,4-D and 0.264 mg/l ABA. After culturing in the light for 87 days, each callus with mature embryoids was transferred to modified third medium containing 0.005 mg/l IBA and 0.2 mg/l BA. Culturing on this medium was performed for 41 days in the light with a transfer to fresh medium containing the same hromones with 0.03464 mg/l GA$_3$. These were cultured in the light for shoot maturation.

While the invention has been described in connection with specific embodiments thereof, it will be understood that it is capable of further modifications. This application is intended to cover any variations, uses or adaptations of the invention following, in general, the principles of the invention and including such departures from the present disclosure as come within known and customary practice within the art to which the invention pertains.

We claim:

1. A process for regenerating soybean plantlets from cell or tissue culture which comprises the steps of:

(a) culturing tissue obtained from the immature embryo of a soybean plant, Glycine max, on a first medium which comprises the MS mineral salts modified so that the concentration of iron (II) sulfate heptahydrate is 41.7 mg/l and the concentration of disodium EDTA is 55.9 mg/l, Nitsch's vitamins modified so that the concentration of thiamine is 0.9 mg/l, 100 mg/l myo-inositol, 2%–3% sucrose, and a hormone selected from the group consisting of (1) 0.5–10.0 mg/l 2,4-D, (2) a mixture of 1–3 mg/l IAA and 3–10 mg/l 2,4-D and (3) a mixture of 1–3 mg/l IAA, 3–10 mg/l 2,4-D and 0.0264–0.264 mg/l ABA to ensure callus and embryoid formation, (b) subculturing said callus with embryoids on a second medium which comprises the MS mineral salts modified so that the concentration of iron (II) sulfate heptahydrate is 41.7 mg/l and the concentration of disodium EDTA is 55.9 mg/l, Nitsch's vitamins modified so that the concentration of thiamine is 0.9 mg/l, 100 mg/l myo-inositol, 2%–3% sucrose, and a hormone selected from the group consisting of (1) 3–5 mg/l 2,4-D, (2) a mixture of 1–3 mg/l IAA and 3–10 mg/l 2,4-D, (3) a mixture of 1.0–2.0 mg/l IAA and 0.5–1.0 mg/l t-zeatin, (4) a mixture of 1.0–2.0 mg/l IAA and 2.73–5.46 mg/l adenine sulfate, (5) a mixture of 100–1000 mg/l casein hydrolysate, 1.0–2.0 mg/l IAA, 0.5–1.0 mg/l t-zeatin, 0.0097–0.0606 mg/l picloram and 0.0264–1.32 mg/l ABA, and (6) a mixture of 3–5 mg/l 2,4-D, 1–3 mg/l IAA and 0.0264–0.264 mg/l ABA to ensure embroyid formation;

(c) subculturing said callus with mature embryoids on a third medium which comprises the MS mineral salts modified so that the concentration of iron (II) sulfate heptahydrate is 41.7 mg/l and the concentration of disodium EDTA is 55.9 mg/l, Nitsch's vitamins modified so that the thiamine concentration is 0.9 mg/l, 100 mg/l myo-inositol, 2%–3% sucrose and a hormone selected from the group consisting of (1) a mixture of 0.1–0.5 mg/l BA and 0.001–0.05 mg/l IBA, (2) a mixture of 1.0–3.0 mg/l IAA and 2.73–10.92 mg/l adenine sulfate, (3) a mixture of 0.1–0.5 mg/l BA, 0.001–0.05 mg/l IBA and 0.03464 mg/l $GA_3$, and (4) a mixture of 0.05 mg/l IAA, 0.05 mg/l BA and 0.03464 mg/l $GA_3$ to ensure shoot formation; and (d) subculturing said callus with shoots on a fourth medium which comprises at least three of the following components: (1) the MS mineral salts modified so that the conconcentration of iron (II) sulfate heptahydrate is 41.7 mg/l and the concentration of disodium EDTA is 55.9 mg/l, (2) Nitsch's vitamins modified so that the thiamine concentration is 0.9 mg/l, 100 mg/l myo-inositol, (3) 1%–3% sucrose, and (4) a hormone selected from the group consisting of (i) 0.1–1.0 mg/l IAA and (ii) 0.1–1.0 mg/l IBA, with the proviso that components (1), (2) and (3) are always present.

2. The process of claim 1 wherein the soybean plant is selected from the group consisting of the Northrup King variety S-18-84-8032-23, Forrest, Corsoy 79, Evans, Gnome and Mitchell 450 cultivars of Glycine max (L.) Merrill.

3. The process of claim 1 wherein the concentrations of said hormones are:

(1) 3–10 mg/l 2,4-D, a mixture of 1–3 mg/l IAA and 3 mg/l 2,4-D, a mixture of 3 mg/l IAA and 5 mg/l 2,4-D, a mixture of 3 mg/l IAA and 10 mg/l 2,4-D, a mixture of 1–3 mg/l IAA, 3 mg/l 2,4-D and 0.264 mg/l ABA, a mixture of 3 mg/l IAA, 5 mg/l 2,4-D and 0.264 mg/l ABA, or a mixture of 3 mg/l IAA, 10 mg/l 2,4-D and 0.264 mg/l ABA in said first medium;

(2) 5 mg/l 2,4-D, a mixture of 2 mg/l IAA and 3 mg/l 2,4-D, a mixture of 1 mg/l IAA and 1 mg/l t-zeatin, a mixture of 1 mg/l IAA and 5.46 mg/l adenine sulfate, a mixture of 100 mg/l casein hydrolysate, 1 mg/l IAA, 1 mg/l t-zeatin, 0.0097 mg/l picloram and 0.0264 mg/l ABA, a mixture of 100 mg/l casein hydrolysate, 1 mg/l IAA, 1 mg/l t-zeatin, 0.0606 mg/l picloram and 0.0264 mg/l ABA, or a mixture of 3 mg/l 2,4-D, 2 mg/l IAA and 0.264 mg/l ABA in said second medium;

(3) a mixture of 0.005 mg/l IBA and 0.2 mg/l BA, a mixture of 3 mg/l IAA and 5.46 mg/l adenine sulfate, a mixture of 3 mg/l IAA and 10.92 mg/l adenine sulfate, a mixture of 0.005 mg/l IBA, 0.2 mg/l BA and 0.03464 mg/1 $GA_3$, or a mixture of 0.05 mg/l IAA, 0.05 mg/l BA and 0.03464 mg/l $GA_3$ in said third medium; and (4) 0.5 mg/l IAA or 0.5 mg/l IBA in said fourth medium.

4. The process of claim 1 wherein the concentration of sucrose is 2% and the pH is 5.8 in said first, second, third and fourth media.

5. The process of claim 3 wherein the concentration of sucrose is 2% and the pH is 5.8 in said first, second, third and fourth media.

6. The process of claim 1 wherein said immature embryo is first grown on an embryo growth medium before culturing on said first medium, said embryo growth medium comprises the MS mineral salts modified so that the concentration of iron (II) sulfate heptahydrate is 41.7 mg/l and the concentration of disodium EDTA is 55.9 mg/l, Nitsch's vitamins modified so that the concentration of thiamine is 0.9 mg/l, 4000 mg/l myo-inositol, amino acids selected from the group consisting of (a) a mixture of 1000 mg/l alanine, 800 mg/l glutamine, 160 mg/l serine, 50 mg/l tryptophan, 575 mg/l proline and 870 mg/l arginine, and (b) a mixture of 500 mg/l alanine, 400 mg/l glutamine, 80 mg/l serine, 25 mg/l tryptophan, 287.5 mg/l proline and 435 mg/l arginine, 10%–12% sucrose and a hormone selected from the group consisting of (1) 0.1–0.5 mg/l IAA, 0.1–1.0 mg/l adenine sulfate and 0.0264–1.320 mg/l ABA, and (2) 0.1–0.5 mg/l 0.1–0.5 mg/l t-zeatin and 0.0264–1.320 mg/l ABA.

7. The process of claim 3 wherein said immature embryo is first grown on an embryo growth medium before culturing on said first medium, said embryo growth medium comprises the MS mineral salts modified so that the concentration of iron (II) sulfate heptahydrate is 41.7 mg/l and the concentration of disodium EDTA is 55.9 mg/l, Nitsch's vitamins modified so that the concentration of thiamine is 0.9 mg/l, 4000 mg/l myo-inositol, amino acids selected from the group consisting of (a) a mixture of 1000 mg/l alanine, 800 mg/l glutamine, 160 mg/l serine, 50 mg/l tryptophan, 575 mg/l proline and 870 mg/l arginine, and (b) a mixture of 500 mg/l alanine, 400 mg/l glutamine, 80 mg/l serine, 25 mg/l tryptophan, 287.5 mg/l proline and 435 mg/l arginine, 10%–12% sucrose and a hormone selected from the group consisting of (1) 0.1–0.5 mg/l IAA, 0.1–1.0 mg/l adenine sulfate and 0.0264–1.320 mg/l ABA, and (2) 0.1–0.5 mg/l IAA, 0.1–0.5 mg/l t-zeatin and 0.0264–1.320 mg/l ABA.

8. A process for regenerating soybean plantlets from cell or tissue culture which comprises the steps of:
(a) culturing tissue obtained from the immature embryo of a soybean plant, *Glycine max*, on a first medium which comprises the MS mineral salts modified so that the concentration of iron (II) sulfate heptahydrate is 41.7 mg/l and the concentration of disodium EDTA is 55.9 mg/l, Nitsch's vitamins modified so that the concentration of thiamine is 0.9 mg/l, 100 mg/l myo-inositol, 2%–3% sucrose, and a hormone selected from the group consisting of (1) 0.5–10.0 mg/l 2,4-D, (2) a mixture of 1–3 IAA and 3–10 mg/l 2,4-D and (3) a mixture of 1–3 mg/l IAA, 3–10 mg/l 2,4-D and 0.0264–0.264 mg/l ABA to ensure callus and embryoid formation,
(b) subculturing said callus with embryoids on a second medium which comprises the MS mineral salts modified so that the concentration of iron (II) sulfate heptahydrate is 41.7 mg/l and the concentration of disodium EDTA is 55.9 mg/l and the source of nitrogen is 20 mM ammonium citrate, Nitsch's vitamins, 100 mg/l myo-inositol, 2%–3% sucrose, and a hormone selected from the group consisting of (1) a mixture of 1.0–2.0 mg/l IAA and 2.73–5.46 mg/l adenine sulfate, and (2) a mixture of 100–1000 mg/l casein hydrolysate, 1.0–2.0 mg/l IAA, 0.5–1.0 mg/l t-zeatin, 0.0097–0.0606 mg/l picloram and 0.0264–1.32 mg/l ABA, to ensure embryoid formation;
(c) subculturing said callus with mature embryoids on a third medium which comprises the MS mineral salts modified so that the concentration of iron (II) sulfate heptahydrate is 41.7 mg/l and the concentration of disodium EDTA is 55.9 mg/l, Nitsch's vitamins modified so that the thiamine concentration is 0.9 mg/l, 100 mg/l myo-inositol, 2%–3% sucrose and a hormone selected from the group consisting of (1) a mixture of 0.1–0.5 mg/l BA and 0.001–0.05 mg/l IBA, (2) a mixture of 1.0–3.0 mg/l IAA and 2.73–10.92 mg/l adenine sulfate, (3) a mixture of 0.1–0.5 mg/l BA, 0.001–0.05 mg/l IBA and 0.03464 mg/l $GA_3$, and (4) a mixture of 0.05 mg/l IAA, 0.05 mg/l BA and 0.03464 mg/l $GA_3$ to ensure shoot formation; and
(d) subculturing said callus with shoots on a fourth medium which comprises at least three of the following components: (1) the MS mineral salts modified so that the concentration of iron (II) sulfate heptahydrate is 41.7 mg/l and the concentration of disodium EDTA is 55.9 mg/l, (2) Nitsch's vitamins modified so that the thiamine concentration is 0.9 mg/l, 100 mg/l myo-inositol, (3) 1%–3% sucrose, and (4) a hormone selected from the group consisting of (i) 0.1–1.0 mg/l IAA and (ii) 0.1–1.0 mg/l IBA, with the proviso that components (1), (2) and (3) are always present.

9. The process of claim 8 wherein the soybean plant is selected from the group consisting of the Northrup King variety S-18-84-8032-23, Forrest, Corsoy 79, Evans, Gnome and Mitchell 450 cultivars of *Glycine max* (L.) Merrill.

10. The process of claim 8 wherein the concentrations of said hormones are:
(1) 3–10 mg/l 2,4-D, a mixture of 1–3 mg/l IAA and 3 mg/l 2,4-D, a mixture of 3 mg/l IAA and 5 mg/l 2,4-D, a mixture of 3 mg/l IAA and 10 mg/l 2,4-D, a mixture of 1–3 mg/l IAA, 3 mg/l 2,4-D and 0.264 mg/l ABA, a mixture of 3 mg/l IAA, 5 mg/l 2,4-D and 0.264 mg/l ABA, or a mixture of 3 mg/l IAA, 10 mg/l 2,4-D and 0.264 mg/l ABA in said first medium;
(2) a mixture of 1 mg/l IAA and 2.73 mg/l adenine sulfate or a mixture of 100 mg/l casein hydrolysate, 1 mg/l IAA, 1 mg/l t-zeatin, 0.0097 mg/l picloram and 0.0264 mg/l ABA in said second medium;
(3) a mixture of 0.005 mg/l IBA and 0.2 mg/l BA, a mixture of 3 mg/l IAA and 5.46 mg/l adenine sulfate, a mixture of 3 mg/l IAA and 10.92 mg/l adenine sulfate, a mixture of 0.005 mg/l IBA, 0.2 mg/l BA and 0.03464 mg/l $GA_3$, or a mixture of 0.05 mg/l IAA, 0.05 mg/l BA and 0.03464 mg/l $GA_3$ in said third medium; and
(4) 0.5 mg/l IAA or 0.5 mg/l IBA in said fourth medium.

11. The process of claim 8 wherein the concentration of sucrose is 2% and the pH is 5.8 in said first, second, third and fourth media.

12. The process of claim 10 wherein the concentration of sucrose is 2% and the pH is 5.8 in said first, second, third and fourth media.

13. The process of claim 8 wherein said immature embryo is first grown on an embryo growth medium before culturing on said first medium, said embryo growth medium comprises the MS mineral salts modified so that the concentration of iron (II) sulfate heptahydrate is 41.7 mg/l and the concentration of disodium EDTA is 55.9 mg/l, Nitsch's vitamins modified so that the concentration of thiamine is 0.9 mg/l, 4000 mg/l myo-inositol, amino acids selected from the group consisting of (a) a mixture of 1000 mg/l alanine, 800 mg/l glutamine, 160 mg/l serine, 50 mg/l tryptophan, 575 mg/l proline and 870 mg/l arginine, and (b) a mixture of 500 mg/l alanine, 400 mg/l glutamine, 80 mg/l serine, 25 mg/l tryptophan 287.5 mg/l proline and 435 mg/l arginine, 10%–12% sucrose and a hormone selected from the group consisting of (1) 0.1–0.5 mg/l IAA, 0.1–1.0 mg/l adenine sulfate and 0.0264–1.320 mg/l ABA, and (2) 0.1–0.5 mg/l IAA, 0.1–0.5 mg/l t-zeatin and 0.0264–1.320 mg/l ABA.

14. The process of claim 10 wherein said immature embryo is first grown on an embryo growth medium before culturing on said first medium, said embryo growth medium comprises the MS mineral salts modified so that the concentration of iron (II) sulfate heptahydrate is 41.7 mg/l and the concentration of disodium EDTA is 55.9 mg/l, Nitsch's vitamins modified so that the concentration of thiamine is 0.9 mg/l, 4000 mg/l myo-inositol, amino acids selected from the group consisting of (a) a mixture of 1000 mg/l alanine, 800 mg/l glutamine, 160 mg/l serine, 50 mg/l tryptophan, 575 mg/l proline and 870 mg/l arginine, and (b) a mixture of 500 mg/l alanine, 400 mg/l glutamine, 80 mg/l serine, 25 mg/l tryptophan, 287.5 mg/l proline and 435 mg/l arginine, 10%–12% sucrose and a hormone selected from the group consisting of (1) 0.1–0.5 mg/l IAA, 0.1–1.0 mg/l adenine sulfate and 0.0264–1.320 mg/l ABA, and (2) 0.1–0.5 mg/l IAA, 0.1–0.5 mg/l t-zeatin and 0.0264–1.320 mg/l ABA.

15. A process for regenerating soybean plantlets from cell or tissue culture which comprises the steps of:
  (a) culturing tissue obtained from the immature embryo of a soybean plant, *Glycine max*, on a first medium which comprises the MS mineral salts modified so that the concentration of iron (II) sulfate heptahydrate is 41.7 mg/l and the concentration of disodium EDTA is 55.9 mg/l, Nitsch's vitamins modified so that the concentration of thiamine is 0.9 mg/l, 4000 mg/l myo-inositol, amino acids selected from the group consisting of (1) a mixture of 1000 mg/l alanine, 800 mg/l glutamine, 160 mg/l serine, 50 mg/l tryptophan, 575 mg/l proline and 870 mg/l arginine, and (2) a mixture of 500 mg/l alanine, 400 mg/l glutamine, 80 mg/l serine, 25 mg/l tryptophan, 287.5 mg/l proline and 435 mg/l arginine, 10%–12% sucrose, and a hormone selected from the group consisting of (1) a mixture of 0.1–0.5 mg/l IAA, 0.1–1.0 mg/l adenine sulfate and 0.0264–1.32 mg/l ABA, and (2) a mixture of 0.1–0.5 mg/l IAA, 0.1–0.5 mg/l t-zeatin and 0.0264–1.32 mg/l ABA to ensure callus and embryoid formation,
  (b) subculturing said callus with embryoids on a second medium which comprises the MS mineral salts modified so that the concentration of iron (II) sulfate heptahydrate is 41.7 mg/l and the concentration of disodium EDTA is 55. mg/l, Nitsch's vitamins modified so that the concentration of thiamine is 0.9 mg/l, 100 mg/l myo-inositol, 2%–3% sucrose, and a hormone selected from the group consisting of (1) 3–5 mg/l 2,4-D, (2) a mixture of 1–3 mg/l IAA and 3–10 mg/l 2,4-D, (3) a mixture of 1.0–2.0 mg/l IAA and 0.5–1.0 mg/l t-zeatin, (4) a mixture of 1.0–2.0 mg/l IAA and 2.73–5.46 mg/l adenine sulfate, (5) a mixture of 100–1000 mg/l casein hydrolysate, 1.0–2.0 mg/l IAA, 0.5–1.0 mg/l t-zeatin, 0.0097–0.0606 mg/l picloram and 0.0264–1.32 mg/l ABA, and (6) a mixture of 3–5 mg/l 2,4-D, 1–3 mg/l IAA and 0.0264–0.264 mg/l ABA to ensure embroyid formation;
  (c) subculturing said callus with mature embryoids on a third medium which comprises the MS mineral salts modified so that the concentration of iron (II) sulfate heptahydrate is 41.7 mg/l and the concentration of disodium EDTA is 55.9 mg/l, Nitsch's vitamins modified so that the thiamine concentration is 0.9 mg/l, 100 mg/l myo-inositol, 2%–3% sucrose and a hormone selected from the group consisting of (1) a mixture of 0.1–0.5 mg/l BA and 0.001–0.05 mg/l IBA, (2) a mixture of 1.0–3.0 mg/l IAA and 2.73–10.92 mg/l adenine sulfate, (3) a mixture of 0.1–0.5 mg/l BA, 0.001–0.05 mg/l IBA and 0.03464 mg/l GA$_3$, and (4) a mixture of 0.05 mg/l IAA, 0.05 mg/l BA and 0.03464 mg/l GA$_3$ to ensure shoot formation; and
  (d) subculturing said callus with shoots on a fourth medium which comprises at least three of the following components: (1) the MS mineral salts modified so that the concentration of iron (II) sulfate heptahydrate is 41.7 mg/l and the concentration of disodium EDTA is 55.9 mg/l, (2) Nitsch's vitamins modified so that the thiamine concentration is 0.9 mg/l, 100 mg/l myo-inositol, (3) 1%–3% sucrose, and (4) a hormone selected from the group consisting of (i) 0.1–1.0 mg/l IAA and (ii) 0.1–1.0 mg/l IBA, with the proviso that components (1), (2) and (3) are always present.

16. The process of claim 15 wherein the soybean plant is selected from the group consisting of the Northrup King variety S-18-84-8032-23, Forrest, Corsoy 79, Evans, Gnome and Mitchell 450 cultivars of *Glycine max* (L.) Merrill.

17. The process of claim 15 wherein the concentrations of said hormones are:
  (1) a mixture of 0.1 mg/l IAA, 1 mg/l adenine sulfate and 1.32 mg/l ABA or a mixture of 0.1 mg/l IAA, 0.2 mg/l t-zeatin and 1.32 mg/l ABA in said first medium,
  (2) 5 mg/l 2,4-D, a mixture of 2 mg/l IAA and 3 mg/l 2,4-D, a mixture of 1 mg/l IAA and 1 mg/l t-zeatin, a mixture of 1 mg/l IAA and 5.46 mg/l adenine sulfate, a mixture of 100 mg/l casein hydrolysate, 1 mg/l IAA, 1 mg/l t-zeatin, 0.0097 mg/l picloram and 0.0264 mg/l ABA, a mixture of 100 mg/l casein hydrolysate, 1 mg/l IAA, 1 mg/l t-zeatin, 0.0606 mg/l picloram and 0.0264 mg/l ABA, or a mixture of 3 mg/l 2,4-D, 2 mg/l IAA and 0.264 mg/l ABA in said second medium;
  (3) a mixture of 0.005 mg/l IBA and 0.2 mg/l BA, a mixture of 3 mg/l IAA and 5.46 mg/l adenine sulfate, a mixture of 3 mg/l IAA and 10.92 mg/l adeine sulfate, a mixture of 0.005 mg/l IBA, 0.2 mg/l BA and 0.03464 mg/l GA$_3$, or a mixture of 0.05 mg/l IAA, 0.05 mg/l BA and 0.03464 mg/l GA$_3$ in said third medium; and
  (4) 0.5 mg/l IAA or 0.5 mg/l IBA in said fourth medium.

18. The process of claim 15 wherein the concentration of sucrose is 2% and the pH is 5.8 in said second, third and fourth media.

19. The process of claim 17 wherein the concentration of sucrose is 2% and the pH is 5.8 in said second, third and fourth media.

20. A process for regenerating soybean plantlets from cell or tissue culture which comprises the steps of:
  (a) culturing tissue obtained from the immature embryo of a soybean plant, *Glycine max*, on a first medium which comprises the MS mineral salts modified so that the concentration of iron (II) sulfate heptahydrate is 41.7 mg/l and the concentration of disodium EDTA is 55.9 mg/l, Nitsch's vitamins modified so that the concentration of thiamine is 0.9 mg/l, 4000 mg/l myo-inositol, amino acids selected from the group consisting of (1) a mixture of 1000 mg/l alanine, 800 mg/l glutamine, 160 mg/l serine, 50 mg/l tryptophan, 575 mg/l proline and 870 mg/l arginine, and (2) a mixture of 500 mg/l alanine, 400 mg/l glutamine, 80 mg/l serine, 25 mg/l tryptophan, 287.5 mg/l proline and 435 mg/l arginine, 10%–12% sucrose, and a hormone selected from the group consisting of (1) a mixture of 0.1–0.5 mg/l IAA, 0.1–1.0 mg/l adenine sulfate and 0.0264–1.32 mg/l ABA, and (2) a mixture of 0.1–0.5 mg/l IAA, 0.1–0.5 mg/l t-zeatin and 0.0264–1.32 mg/l ABA to ensure callus and embryoid formation,
  (b) subculturing said callus with embryoids on a second medium which comprises the MS mineral salts modified so that the concentration of iron (II) sulfate heptahydrate is 41.7 mg/l and the concentration of disodium EDTA is 55.9 mg/l and the source of nitrogen is 20 mM ammonium citrate, Nitsch's vitamins, 100 mg/l myo-inositol, 2%–3% sucrose, and a hormone selected from the group consisting of (1) a mixture of 1.0–2.0 mg/l IAA and 2.73–5.46 mg/l adenine sulfate, and (2) a mixture of 100–1000 mg/l casein hydrolysate, 1.0–2.0 mg/l IAA, 0.5–1.0 mg/l t-zeatin, 0.0097–0.0606 mg/l picloram and 0.0264–1.32 mg/l ABA, to ensure embroyid formation;

(c) subculturing said callus with mature embryoids on a third medium which comprises the MS mineral salts modified so that the concentration of iron (II) sulfate heptahydrate is 41.7 mg/l and the concentration of disodium EDTA is 55.9 mg/l, Nitsch's vitamins modified so that the thiamine concentration is 0.9 mg/l, 100 mg/l myo-inositol, 2%–3% sucrose and a hormone selected from the group consisting of (1) a mixture of 0.1–0.5 mg/1 BA and 0.001–0.05 mg/l IBA, (2) a mixture of 1.0–3.0 mg/l IAA and 2.73–10.92 mg/l adenine sulfate, (3) a mixture of 0.1–0.5 mg/l BA, 0.001–0.05 mg/l IBA and 0.03464 mg/l $GA_3$, and (4) a mixture of 0.05 mg/l IAA, 0.05 mg/l BA and 0.03464 mg/l $GA_3$ to ensure shoot formation; and (d) subculturing said callus with shoots on a fourth medium which comprises at least three of the following components: (1) the MS mineral salts modified so that the concentration of iron (II) sulfate heptahydrate is 41.7 mg/l and the concentration of disodium EDTA is 55.9 mg/l, (2) Nitsch's vitamins modified so that the thiamine concentration is 0.9 mg/l, 100 mg/l myo-inositol, (3) 1%–3% sucrose, and (4) a hormone selected from the group consisting of (i) 0.1–1.0 mg/l IAA and (ii) 0.1–1.0 mg/l IBA, with the proviso that components (1), (2) and (3) are always present.

21. The process of claim 20 wherein the soybean plant is selected from the group consisting of the Northrup King variety S-18-84-8032-23, Forrest, Corsoy 79, Evans, Gnome and Mitchell 450 cultivars of *Glycine max* (L.) Merrill.

22. The process of claim 20 wherein the concentrations of said hormones are:
(1) a mixture of 0.1 mg/l IAA, 1 mg/l adenine sulfate and 1.32 mg/l ABA or a mixture of 0.1 mg/l IAA, 0.2 mg/l t-zeatin and 1.32 mg/l ABA in said first medium,
(2) a mixture of 1 mg/l IAA and 2.73 mg/l adenine sulfate or a mixture of 100 mg/l casein hydrolysate, 1 mg/l IAA, 1 mg/l t-zeatin, 0.0097 mg/l picloram and 0.0264 mg/l ABA in said second medium;
(3) a mixture of 0.005 mg/l IBA and 0.2 mg/l BA, a mixture of 3 mg/l IAA and 5.46 mg/l adenine sulfate, a mixture of 3 mg/l IAA and 10.92 mg/l adenine sulfate, a mixture of 0.005 mg/l IBA, 0.2 mg/l BA and 0.03464 mg/l $GA_3$, or a mixture of 0.05 mg/l IAA, 0.05 mg/l BA and 0.03464 mg/l $GA_3$ in said third medium; and
(4) 0.5 mg/l IAA or 0.5 mg/l IBA in said fourth medium.

23. The process of claim 20 wherein the concentration of sucrose is 2% and the pH is 5.8 in said second, third and fourth media.

24. The process of claim 22 wherein the concentration of sucrose is 2% and the pH is 5.8 in said second, third and fourth media.

* * * * *

UNITED STATES PATENT AND TRADEMARK OFFICE
CERTIFICATE OF CORRECTION

PATENT NO. : 4,684,612

DATED : August 4, 1987

INVENTOR(S) : John K. HEMPHILL et al.

It is certified that error appears in the above-identified patent and that said Letters Patent is hereby corrected as shown below:

```
In Claim 1, column 17, line 41,
   Claim 8, column 19, lines 40-41,
   Claim 15, column 21, line 45, and
   Claim 20, column 23, lines 9-10, change "formation" to -- maturation --.
```

Signed and Sealed this

Twenty-sixth Day of July, 1988

Attest:

DONALD J. QUIGG

Attesting Officer

Commissioner of Patents and Trademarks